United States Patent
Cunningham

(10) Patent No.: US 7,540,988 B2
(45) Date of Patent: Jun. 2, 2009

(54) METHOD FOR MAKING HOLDER

(75) Inventor: Chris Cunningham, Buckinghamshire (GB)

(73) Assignee: PerkinElmer International C.V. (CH)

( * ) Notice: Subject to any disclaimer, the term of this patent is extended or adjusted under 35 U.S.C. 154(b) by 663 days.

(21) Appl. No.: 11/214,157

(22) Filed: Aug. 29, 2005

(65) Prior Publication Data

US 2005/0280180 A1 Dec. 22, 2005

Related U.S. Application Data

(62) Division of application No. 10/438,125, filed on May 14, 2003, now Pat. No. 7,121,519.

(30) Foreign Application Priority Data

May 14, 2002 (EP) .................................. 02253344

(51) Int. Cl.
  *B29C 45/14* (2006.01)
(52) U.S. Cl. ....................... 264/278; 264/275
(58) Field of Classification Search ............ 427/8, 427/133; 264/259, 271.1, 275, 278
  See application file for complete search history.

(56) References Cited

U.S. PATENT DOCUMENTS

| 4,027,845 A | * | 6/1977 | Putzer ........................ 249/142 |
| 4,040,597 A | * | 8/1977 | Pierson et al. .............. 249/134 |
| 4,076,791 A | | 2/1978 | Barter et al. ........... 264/272.15 |
| 4,100,958 A | * | 7/1978 | Workman .................. 164/7.2 |
| 4,301,857 A | * | 11/1981 | Rushforth .................. 164/416 |
| 4,470,786 A | * | 9/1984 | Sano et al. ................ 425/125 |
| 4,986,965 A | * | 1/1991 | Ushikubo .................. 422/102 |
| 5,364,580 A | * | 11/1994 | Prent ......................... 264/138 |
| 5,814,695 A | | 9/1998 | Fitzgerald et al. ........... 524/731 |
| 5,922,099 A | * | 7/1999 | Yoon et al. .................... 65/395 |
| 5,938,993 A | | 8/1999 | Greene ...................... 264/46.4 |
| 2007/0266662 A1 | * | 11/2007 | Oram et al. ................ 52/311.1 |

FOREIGN PATENT DOCUMENTS

| EP | 0 767 369 A2 | 4/1997 |
| EP | 0 896 215 A1 | 2/1999 |
| EP | 896215 A1 * | 2/1999 |
| GB | 414789 | 8/1934 |

OTHER PUBLICATIONS

European Search Report and Abstract for EP 02253344.2, Oct. 23, 2002, 4 pp.

* cited by examiner

*Primary Examiner*—Joseph S. Del Sole
*Assistant Examiner*—David N Brown, II
(74) *Attorney, Agent, or Firm*—St. Onge Steward Johnston & Reens LLC

(57) ABSTRACT

A method is disclosed of making a mounting or holder for use in analysis in an analytical instrument of samples of similar shape. The method includes obtaining a moulding that includes a protrusion; securing a sample having a lower surface and a side surface to the top of the protrusion of the moulding; introducing a mouldable material into the moulding only up to a level that is along the side surface of the sample and above the lower surface of the sample; allowing the mouldable material to set to form a mounting or holder; and separating the mounting or holder from the sample and the moulding.

8 Claims, 2 Drawing Sheets

ID OF HOLDER

CROSS REFERENCE TO RELATED APPLICATIONS

This application is a divisional of co-pending U.S. application Ser. No.10/438,125 for "Silicone Mould Tool", filed on May 14, 2003 now U.S. Pat. No. 7,121,519.

FIELD OF THE INVENTION

The present invention relates to a tool assembly which can be used to make a mounting or holder for a tablet-shaped sample which is to undergo analysis.

Analytical instruments such as FT-IR spectrometers are used to analyze samples. One type of sample which requires analysis in such an instrument is a tablet-shaped sample. Many pharmaceutical products are sold in the form of tablets. The manufacturers of such tablets are required to test those tablets in order to ensure that they meet the required specifications for content and concentration. One known way of testing such a tablet is to grind the tablet into a powder, dissolve it in a liquid and then analyze the resulting solution. More recently, systems have been developed which enable the tablet to be analyzed intact. In such a system a tablet is typically held in a V-shaped device by means of spring pressure and then located in an analytical instrument such as an FT-IR spectrometer for analysis in a known way. This procedure works well for round tablets, but is not satisfactory for irregularly shaped tablets and furthermore it is not always possible with such an arrangement to hold a series of tablets in a consistent and reproducible way.

It is also known to provide a holder machined out of metal which can receive a sample for analysis. However, the holder can only receive a tablet of a particular shape and if different shaped tablets are to be analyzed then a new holder needs to be obtained.

The present invention is concerned with a tool assembly which obviates all the abovementioned problems and enables a user of an analytical instrument to make their own holders or to have them made more cheaply.

According to the present invention there is provided a tool for making a mounting or holder for a tablet-shaped sample which is to undergo analysis in an analytical instrument, said tool comprising a moulding which defines a lower surface and a side wall or walls, and a pin which, in use, extends upwardly above the lower surface of the moulding, the arrangement being such that in use a tablet is mounted on the upper end of the pin and mouldable material is introduced into the moulding so that it locates around the lower part of the tablet.

After the mouldable material has set, a mounting or holder results which has a recess in its upper surface that matches the shape of the tablet and can therefore be used to support similar tablets in an analytical instrument such an FT-JR spectrometer.

The tool may comprise a base and a moulding. The pin may locate through a hole in the base member and a hole in the lower wall of the moulding. The moulding may be formed from silicone. The mouldable material be may be loaded resin such as loaded polyurethane. According to another aspect of the present invention, there is provided a method of making a mounting or holder for a tablet-shaped sample using a tool as defined above, said method comprising, securing a tablet to the upper end of the pin, introducing mouldable material into the moulding until it locates around a lower surface of the tablet, and allowing the mouldable material to solidify or set.

BRIEF DESCRIPTION OF DRAWINGS

The invention will be described by way of example only, with particular reference to the accompanying drawings. In the drawings.

DETAILED DESCRIPTION OF DRAWINGS

Figure 1:
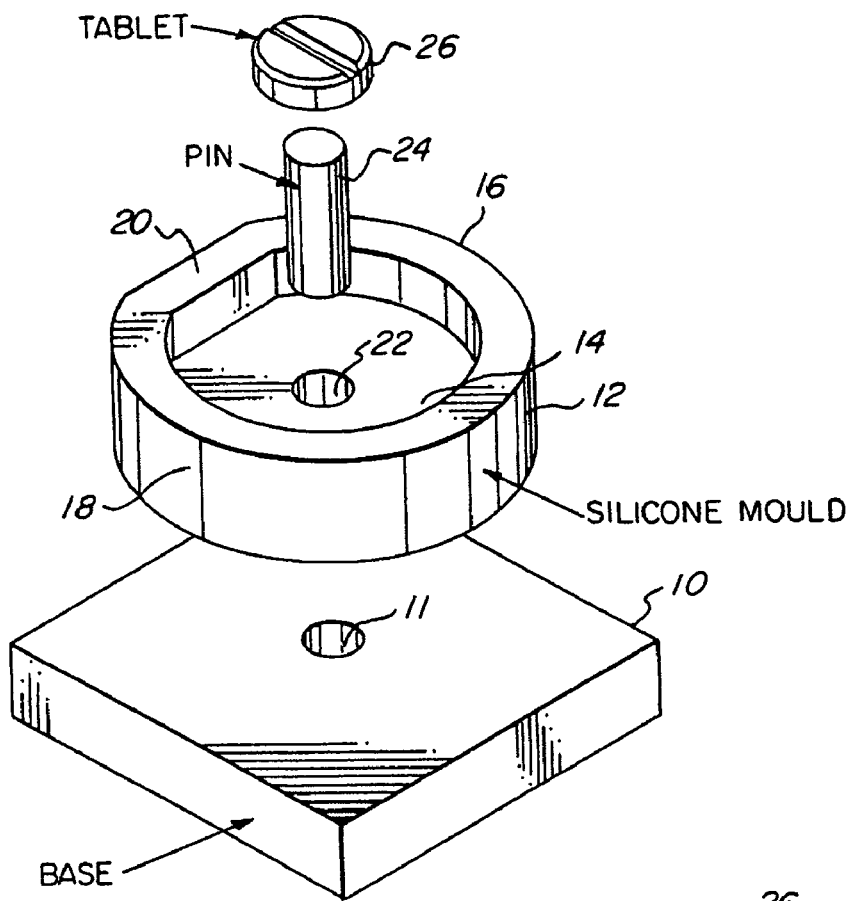
FIG. 1 is a perspective view showing a tool assembly in accordance with the present invention.

Referring to the drawings, a tool assembly comprises a base element (10). The base element (10) is generally square-shaped and can be made from any suitable rigid material. The base element (10) has a central through hole (11).

The tool assembly also includes a moulding (12). The moulding (12) is formed from silicone. The moulding (12) has a lower wall (14) and an upstanding side wall (16). The upstanding side wall is part circular as shown at (18) and part linear as shown at (20). The lower wall (14) of the moulding has a central through aperture (22), the diameter of which is substantially the same as that of the hole (11) in the base.

The tool assembly also includes a pin (24) whose radial dimensions are such that it can locate snugly within the hole (22) and the hole (11).

Figure 2A:
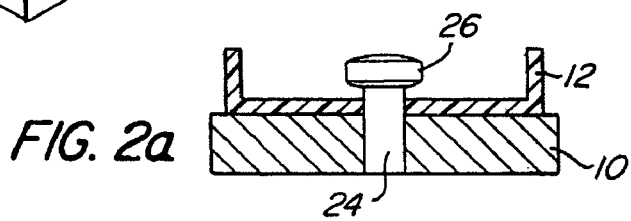
FIGS. 2*a* to 2*c* illustrate the steps which are carried out in order to form a mounting or holder.
Figure 2B:
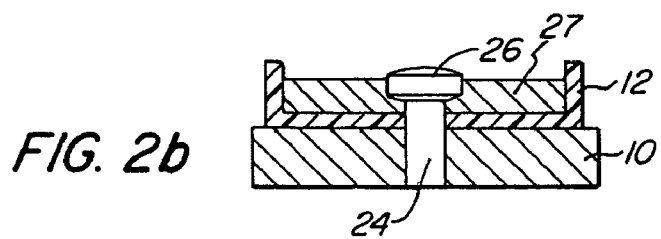

In use, a tablet (26) for which a holder or mounting is to be produced, is secured to the upper end of the pin (24) by means of a suitable adhesive, such as Superglue. The tablet is then painted with a suitable release agent. The pin/tablet assembly is then pushed into the silicone mould so that the pin (24) protrudes from the underside of the moulding into the base (10) as shown in FIG. 2*a* of the drawings. The assembly is then placed upon a flat surface with the lower end of the pin resting on the surface. Then mouldable material (27), such as loaded polyurethane, is introduced into the moulding (12), as shown in FIG. 2*b* of the drawings. The mouldable material is introduced until as shown in FIG. 2*b* it covers slightly more than half of the surface of the tablet (26). As an alternative to the abovementioned procedure, the initial step may comprise locating the pin and tablet assembly only partly into the hole in the base (10), introducing the mouldable material into the moulding (12) and then pushing the pin-tablet assembly into the base element (10) until the lower end of the pin (24) locates against the flat surface as shown in FIG. 2*b* of the drawings.

After the above steps have been carried out, the mouldable material is then allowed to cure, following which the tablet-pin assembly is pushed up and out of the base and moulding. This will be assisted by the fact that the tablet had previously been coated with a release agent. The completed holder can then be removed from the silicone mould.

Figure 2C:
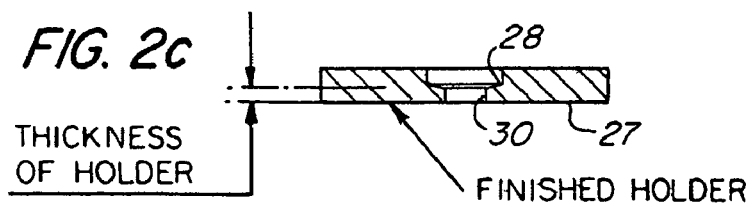
Figure 3:
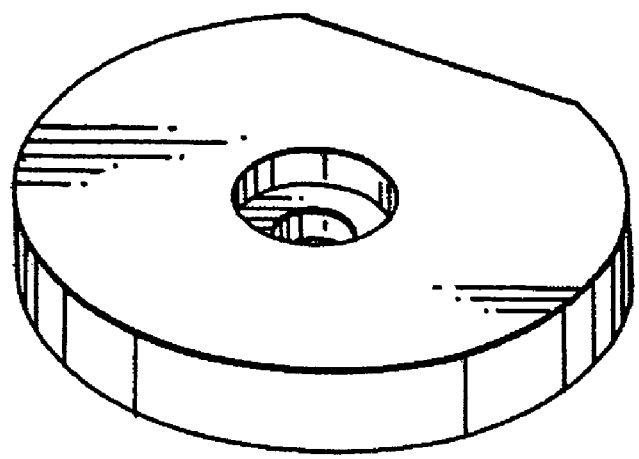
FIG. 3 is a perspective view of a completed moulding.

As shown in FIG. 2*c*, the holder (27) has a depression or recess (28) which matches the shape of the tablet used to produce it. Therefore other tablets of the same shape and dimension can be located precisely in the recess. Additionally, the holder has a hole (30) which allows the tablet to be exposed to an analyzing beam when placed in the analytical instrument. The structure of the holder (27) is such that radiation from the analyzing beam, when the holder is in the instrument, is prevented from leaking around the side of the tablet, because of the fact that the holder is an excellent fit around the tablet and the hole size (30), which allows the analyzing radiation to impinge upon the tablet, is significantly smaller than the tablet being tested.

It will be appreciated that in forming the holder (27) the height of the tablet from the bottom of the holder is in effect controlled by appropriately selecting the length of the pin (24) and the thickness of the base and the thickness of the silicone moulding.

It will be appreciated that the tool assembly described above can be used by an operator of an analytical instrument such as an FT-IR spectrometer in order to produce holders for a wide range of tablet size and shapes. The user of such an instrument can in a very simple manner make their own tablet holders and such holders can be made accurately and in such a way as to ensure that the tablets can be located successively into an analytical instrument in a reproducible manner.

Figure 4:
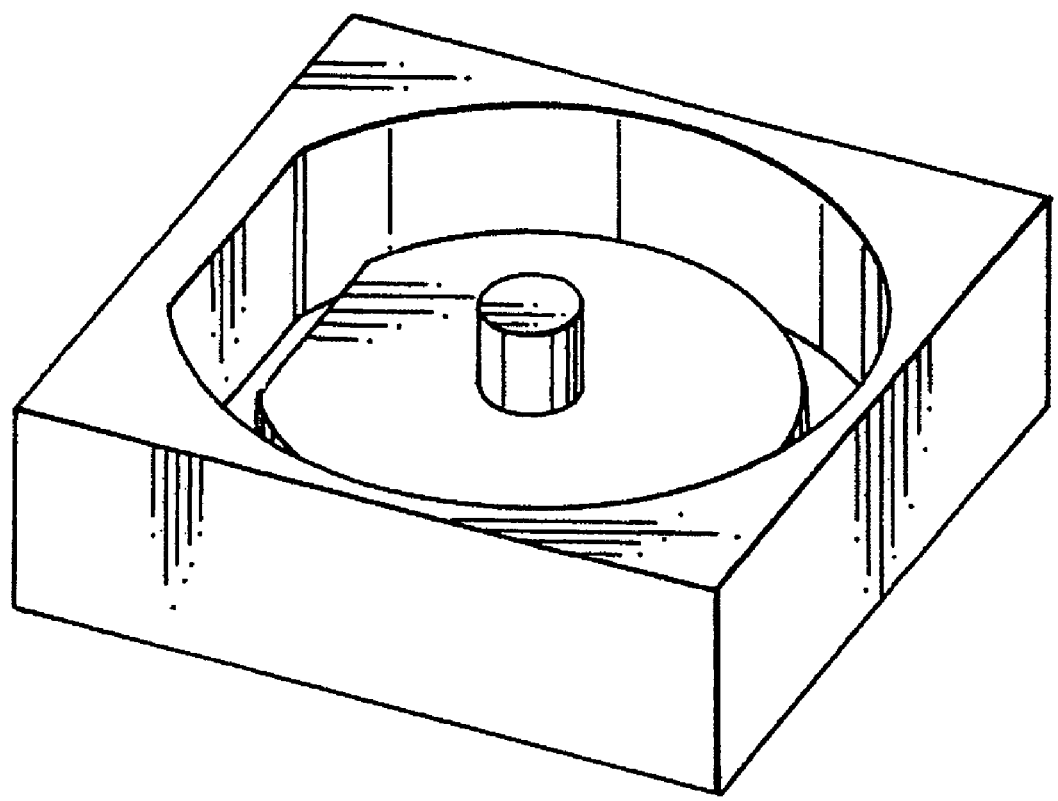
FIG. 4 shows a tool which can be used to make a silicone mould.

FIG. 4 is a view of tool which can be used to make the silicone moulding (12).

The invention claimed is:

1. A method of making a mounting or holder for a tablet-shaped sample using a tool comprising a moulding which defines a lower surface and a side wall or walls, and a pin which, in use, extends upwardly above the lower surface of the moulding, the arrangement being such that in use a tablet is mounted on the upper end of the pin and mouldable material is introduced into the moulding so that it locates around the lower part of the tablet, said method comprising securing a tablet to the upper end of the pin, introducing mouldable material into the moulding until it locates around a lower surface of the tablet, and allowing the mouldable material to solidify or set.

2. A method of making a mounting or holder for use in analysis in an analytical instrument of samples of similar shape, said method comprising:
   (a) providing a moulding that includes a protrusion;
   (b) securing a tablet-shaped sample having a lower surface and a side surface to the top of the protrusion of the moulding;
   (c) introducing a mouldable material into the moulding only up to a level that
   is along the side surface of the sample and above the lower surface of the sample; (d) allowing the mouldable material to set to form a mounting or holder; and (e) separating the mounting or holder from the sample and the moulding.

3. A method according to claim 2 wherein a loaded resin is introduced into the moulding.

4. A method according to claim 2 wherein loaded polyurethane is introduced into the moulding.

5. A method according to claim 2 wherein a moulding made of silicone is provided.

6. A method according to claim 2 further comprising placing the mounting or holder in the vicinity of an analytical instrument.

7. A method according to claim 6 further comprising placing a sample of shape similar to the sample used during creation of the mounting or holder into a recess in the mounting or holder.

8. A method according to claim 7 further comprising allowing the sample to undergo analysis by the analytical machine.

* * * * *